(12) United States Patent
Bischoff et al.

(10) Patent No.: US 9,029,767 B2
(45) Date of Patent: May 12, 2015

(54) METHOD FOR ADJUSTING A STEM EQUIPPED WITH AN ABERRATION CORRECTOR

(71) Applicant: FEI Company, Hillsboro, OR (US)

(72) Inventors: Maarten Bischoff, Uden (NL); Bernd Rieger, Delft (NL)

(73) Assignee: FEI Company, Hillsoboro ( * ) Notice: Subject to any disclaimer, the term of this patent is extended or adjusted under 35 U.S.C. 154(b) by 79 days.

(21) Appl. No.: 13/655,672

(22) Filed: Oct. 19, 2012

(65) Prior Publication Data

US 2013/0105689 A1    May 2, 2013

Related U.S. Application Data

(60) Provisional application No. 61/548,961, filed on Oct. 19, 2011.

(30) Foreign Application Priority Data

Oct. 19, 2011   (EP) ..................................... 11185734

(51) Int. Cl.
*G01N 23/20* (2006.01)
*H01J 37/21* (2006.01)
(Continued)

(52) U.S. Cl.
CPC ................. *H01J 37/22* (2013.01); *G01N 23/20* (2013.01); *H01J 37/153* (2013.01); *H01J 37/20* (2013.01); *H01J 37/265* (2013.01); *H01J 37/28* (2013.01); *H01J 2237/1532* (2013.01); *H01J 2237/1534* (2013.01); *H01J 2237/216* (2013.01); *H01J 2237/221* (2013.01); *H01J 2237/2802* (2013.01)

(58) Field of Classification Search
CPC . H01J 37/153; H01J 2237/1534; H01J 37/21; H01J 37/27; H01J 2237/216; H01J 2237/221; H01J 2237/2823; H01J 2237/2802; H01J 2237/223; H01J 2237/2826; H01J 37/20; H01J 2237/201; H01J 2237/20
USPC .................................. 250/311, 252, 1, 440.11
See application file for complete search history.

(56) References Cited

U.S. PATENT DOCUMENTS 5,084,622 A    1/1992   Rose
5,300,776 A *  4/1994   Krivanek ....................... 250/311
(Continued)

OTHER PUBLICATIONS

Cowley (Book Section, 978-1-4020-8003-6, Handbook of Microscopy for Nanotechnology, Yao, Nan, Wang, ZhongLin, Chapter "Scanning Transmission Electron Microscopy" Springer US, Jan. 1, 2001, Cowley, J.M., pp. 455-491).*

(Continued)

*Primary Examiner* — Brooke Purinton
(74) *Attorney, Agent, or Firm* — Scheinberg & Associates, PC; Michael O. Scheinberg; John B. Kelly (57) ABSTRACT

The invention relates to a method for adjusting a $C_s$ corrector in a STEM using a crystalline sample. The method comprises recording a through-focus series, converting the obtained images to Fourier space, thus forming a set of images alike diffraction images. By then determining the symmetry of the Fourier images, the corrector can be tuned for better symmetry, and the transfer limit can be determined by determining the maximum distance of the spots from the center. By repeatedly performing these steps, the corrector can be tuned to its optimum performance.

9 Claims, 4 Drawing Sheets

(51) Int. Cl.
*H01J 37/22* (2006.01)
*H01J 37/153* (2006.01)
*H01J 37/20* (2006.01)
*H01J 37/26* (2006.01)
*H01J 37/28* (2006.01)

(56) References Cited

U.S. PATENT DOCUMENTS

| | | | |
|---|---|---|---|
| 5,838,011 | A | 11/1998 | Krijn et al. |
| 5,986,269 | A | 11/1999 | Krijn et al. |
| 6,184,975 | B1 | 2/2001 | Henstra et al. |
| 6,191,423 | B1 | 2/2001 | Krijn et al. |
| 6,246,058 | B1 | 6/2001 | Tiemeijer |
| 6,552,340 | B1 | 4/2003 | Krivanek et al. |
| 6,570,156 | B1 * | 5/2003 | Tsuneta et al. ............... 250/311 |
| 6,616,784 | B2 * | 9/2003 | Chang et al. .................. 250/311 |
| 6,992,289 | B2 | 1/2006 | Maes et al. |
| 7,060,986 | B2 | 6/2006 | Nakamura et al. |
| 7,378,667 | B2 | 5/2008 | Henstra |
| 7,544,939 | B2 | 6/2009 | van der Zande et al. |
| 7,619,220 | B2 * | 11/2009 | Sawada et al. ............... 250/311 |
| 7,915,584 | B2 | 3/2011 | Tiemeijer et al. |
| 8,447,133 | B2 | 5/2013 | Rieger et al. |
| 8,878,130 | B2 * | 11/2014 | Inada et al. .................. 250/310 |
| 2003/0001102 | A1 * | 1/2003 | Zach ............................. 250/311 |
| 2007/0158568 | A1 * | 7/2007 | Nakamura et al. ............ 250/311 |
| 2008/0290264 | A1 | 11/2008 | Henstra et al. |
| 2009/0065708 | A1 * | 3/2009 | Moon et al. ............... 250/440.11 |
| 2010/0032565 | A1 * | 2/2010 | Thust et al. .................. 250/311 |
| 2010/0038557 | A1 * | 2/2010 | Zach ....................... 250/440.11 |
| 2010/0072366 | A1 | 3/2010 | Tiemeijer et al. |
| 2010/0230584 | A1 * | 9/2010 | Niebel et al. ............ 250/442.11 |
| 2011/0114852 | A1 | 5/2011 | Henstra |
| 2013/0062520 | A1 | 3/2013 | Henstra et al. |
| 2013/0266240 | A1 | 10/2013 | Rieger et al. |

OTHER PUBLICATIONS

Uhlemann, Stephan, et al., 'Residual wave aberrations in the first spherical aberration corrected transmission electron microscope,' Ultramicroscopy, 1998, pp. 109-119, vol. 72.

Baba, Norio, et al., 'An auto-tuning method for focusing and astigmatism correction in HAADF-STEM, based on the image contrast transfer function,' Journal of Electron Microscopy, Jan. 1, 2001, pp. 163-176, vol. 50, No. 3.

Haider, M., et al., 'Prerequisites for a Cc/Cs-corrected ultrahigh resolution TEM,' Ultramicroscopy, 2008, pp. 167-178, vol. 108.

Lupini, Andrew R., et al., 'Rapid autotuning for crystalline specimens from an inline hologram,' Journal of Electron Microscopy, Nov. 6, 2008, pp. 195-201, vol. 57, No. 6.

* cited by examiner

METHOD FOR ADJUSTING A STEM EQUIPPED WITH AN ABERRATION CORRECTOR

This application claims priority from U.S. Provisional Application 61/548,961, filed Oct. 19, 2011, which is hereby incorporated by reference.

The invention relates to a method for adjusting a Scanning Transmission Electron Microscope (STEM), said STEM equipped with an objective lens and an aberration corrector for correcting aberrations of the objective lens, the corrector excited with an excitation, and the objective lens focused to a focal value F.

The invention further relates to a sample carrier for performing said method, and the use of such a sample carrier for carrying out the method according to the invention.

As known to the person skilled in the art, high-end STEM's are equipped with correctors for correcting the spherical aberration of the objective lens. Such a corrector is available from e.g. CEOS Gmbh., Heidelberg, Germany (CEOS), and integrated in commercially available STEM's such as the Titan 80-300 of FEI, Hillsboro, Oreg., USA.

Such STEM's are used to image samples, for example samples from crystalline material. Such a sample can be a semiconductor sample, but also a sample of, or at least comprising, crystalline carbon such as e.g. graphene or diamond, with or without inclusions and stacking errors. Resolutions of less than 50 pm (0.5 angstrom) are obtained, resolving for example the dumbbell pair of germanium atoms separated by 47 pm when viewed along the direction.

A problem with such corrected microscopes is that it is almost impossible to adjust the microscope to the required level. By eliminating the spherical aberration of the objective lens, residual aberrations such as coma, two- and three-fold astigmatism dominate the aberrations and lead to a deterioration of the image. For the most advanced instruments, aiming at a resolution of, for example, 50 pm, even experienced operators have significant problems in adjusting the instrument to such a level that the best performance can be achieved. In practice, experienced operations even have major difficulties obtaining 80% of the specified resolution (for example, 60 pm) in a controlled way, leading to adoption of trial-and-error methods which apart from inefficient also requires the sample to receive an increased dose leading to sample contamination or sample damage.

Several methods try to address the problem of eliminating residual aberrations for these high-end STEM's. Most of these methods rely on the use of so-called Ronchigrams. A Ronchigram is a shadow projection of an object, with the cross-over of the illuminating beam a distance from the object. Typically a Ronchigram in a STEM uses a focal plane (cross-over distance) of between 0.5 μm and 1 μm from the sample. The shadow image will show position dependent variations in magnification, From these variations in local magnification aberrations can be derived.

One such method is known from "Rapid autotuning for crystalline specimens", A. R. Lupini et al., Journal of Electron Microscopy, Vol. 57, No. 6 (2008) pp. 15-201. In this publication a method is described in which one or more images of a crystalline sample are recorded. Each of the images is divided in a number of sub-images (patches), for example 9*9 sub-images, and the sub-images are transformed in reciprocal space (also known as Fourier space) using Discrete Fourier Transform. This results in a series of transformed sub-images from which periodicity can be determined, and thus magnification.

It is noted that a representation of a crystalline sample in reciprocal space resembles a diffraction pattern and will show a number of spots, indicating said periodicity.

By comparing the distance of the spots, the variation of the local magnification is determined, which in turn is contributed to different aberrations.

It is noted that the differences in magnification in x and y (or as an alternative in r and ϕ) may differ, and that the difference in magnification is normally expressed as a place dependent vector, not as a scalars.

Lupini mentions in his article that 3-fold astigmatism ($A_2$) and coma ($B_2$) are measured with a standard deviation in the order of tens of nanometers, and that the value of $C_3$ was measured with an accuracy of several μm. Lupini also mentions that these standard deviations are of a similar order as those derived from, in applicants opinion, leading commercially available software packages of CEOS and NION (NION Co., Kirkland, Wash., USA).

It is noted that the use of Ronchigrams is also known to be used for amorphous samples, see for example U.S. Pat. No. 6,552,340. However, in that case not the periodicity of the sample can be used, but other techniques, such as autocorrelation, must be used to determine local magnification differences.

Unfortunately the success of these methods is, as mentioned before, still limited, as shown in table 1. This table shows the maximum allowable aberration coefficients to attain the so-called π/4 limit. Both the π/4 limit and the aberration polynomials as used here are discussed in "Residual wave aberrations in the first spherical corrected transmission electron microscope", S. Uhlemann et al., Ultramicroscopy 72 (1998), pp. 109-119, hereby included by reference. The table 1 given here differs from the table 1 in said publication in that resolution and acceleration voltage differ. However, the way in which the numbers are calculated is identical. The table given here further shows the errors typically obtained with state of the art automated methods. The 'problem' areas are shown in bold, italics, underlined script.

TABLE 1 allowed maximum aberration coefficient limits to attain the π/4 limit at an acceleration voltage of 300 kV, and best (automated) practice.

| Aberration | | Resolution [pm] | | | | Accuracy of automated methods |
|---|---|---|---|---|---|---|
| | | 80 | 70 | 60 | 50 | |
| Defocus | $C_1$ [nm] | *__0.81__* | *__0.62__* | *__0.46__* | *__0.32__* | 1 |
| Twofold astigmatism | $A_1$ [nm] | *__0.81__* | *__0.62__* | *__0.46__* | *__0.32__* | 1 |
| Threefold astigmatism | $A_2$ [nm] | 49.5 | 33.2 | 20.9 | *__12.1__* | 20 |
| Axial coma | $B_2$ [nm] | 16.5 | 11.1 | *__6.96__* | *__4.03__* | 10 |
| Spherical aberration | $C_3$ [μm] | 2.68 | 1.57 | 0.85 | *__0.41__* | 0.5 |
| Fourfold astigmatism | $A_3$ [μm] | 2.68 | 1.57 | 0.85 | 0.41 | 0.1 |
| Star aberration | $S_3$ [μm] | 0.67 | 0.39 | 0.21 | 0.10 | 0.1 |
| Fivefold astigmatism | $A_4$ [μm] | 136 | 69.8 | 32.2 | 13.0 | 2 |
| Axial coma | $B_4$ [μm] | 27.2 | 14.0 | 6.46 | 2.59 | 2 |
| Three lobe aberration | $D_4$ [μm] | 27.2 | 14.0 | 6.46 | 2.59 | 2 |
| Spherical aberration | $C_5$ [mm] | 6.63 | 2.97 | 1.18 | 0.40 | 0.2 |
| Sixfold astigmatism | $A_5$ [mm] | 6.63 | 2.97 | 1.18 | 0.40 | 0.05 |

It is noted that a similar, but even more extensive list of allowed aberration coefficient is given in "Prerequisites for a $C_c/C_s$-corrected ultrahigh-resolution TEM", M. Haider et al., UltraMicroscopy (2007), doi:10.1016/j.ultramic.2007.07.007, more specifically in Table 1 thereof.

That for automated methods e.g. $C_1$ (the defocus) has an error of 1 nm, implies that the automated method will result in a setting with a $C_1$ coefficient of less than or equal to 1 nm, but that it is unlikely to be less than 0.3 nm, as is needed for a resolution of 50 pm.

Another problem with the known method is that the aberrations are measured at a defocus from the sample. After nulling the aberrations, the lens should then be focused on the sample plane (as mentioned before this is already difficult enough), and the refocusing may result in changes of the aberrations, and thus introduction of aberrations.

Another method for correcting aberrations is described in U.S. Pat. No. 7,060,986, in which a through focus series of images is made and by deconvolution the beam profile is determined. The deconvolution is done by e.g. autocorrelating the images. This method is used in the earlier mentioned commercially available package of CEOS, and typically results in accuracies as shown in table 1, right column.

It is noted that the method of U.S. Pat. No. 7,060,986 must be performed on a test specimen, such as a cross-grating. After minimizing the aberration on this cross-grating, a real specimen to be investigated has to be inserted in the microscope. This will take typically one hour. This amount of time, as well as the insertion process, typically lead to a change of settings (for example due to drift or thermal changes) that such an extend that aberrations are limiting the resolution again.

The aim of the invention is to provide a method in which the STEM can be routinely and preferably automatically adjusted to a sufficient level at a setting in which HR-images can be obtained.

To that end the method according to the invention is characterized in that the method comprises the repeated steps of:
a) recording a through-focus series of high-resolution STEM images $I_1 \ldots I_n$ of a crystalline or poly-crystalline part of a sample, the through-focus series covering a defocus range,
b) transforming said images to representations $R_1 \ldots R_n$ in reciprocal space, the representations showing a number of spots arranged in a pattern, each of the spots showing an intensity,
c) for each of the representations $R_1 \ldots R_n$ determine the asymmetry in intensity of at least part of the spots
d) change the excitation of the corrector and the focal value F of the objective lens, combining knowledge of the aberration corrector with said asymmetry,
e) optionally change the defocus range, and
f) optionally record a high-resolution STEM image using the altered values of excitation and/or focus, transform said image to a representation in reciprocal space and determine the symmetry of said representation as well as the distance from the centre of the pattern at which spots can be observed, said distance giving an indication of the maximum transfer limit,
said repetition of steps aborted when:
the changes in excitation of corrector and objective lens are below predetermined values, and/or
the optionally recorded in-focus image shows a symmetry better than a predetermined value and a maximum transfer limit higher than a predetermined transfer limit, and/or
the number of repetitions exceeds a predetermined maximum number of repetitions.

Inventors found that for a crystalline or poly-crystalline sample, the representation in reciprocal space resembles a diffraction pattern. As known to the person skilled in the art, such a conversion can be the result of a Fourier transform, but other transforms giving a representation in reciprocal space are known as well.

It is noted that in many cases the position of the spots relative to each other is known, because the lattice of the crystal is known.

It is mentioned that since the initial discovery of crystal-like individual arrays of atoms that are not regularly repeated, in 1982 the acceptance of the concept and the word quasicrystal have led the International Union of Crystallography to redefine the term crystal to mean "any solid having an essentially discrete diffraction diagram", thereby shifting the essential attribute of crystallinity from image space to reciprocal space. Therefore in this context the definition crystal comprises the earlier mentioned quasi-crystals, such as the icosahedral Zn—Mg—Ho quasicrystal.

A big advantage of the method according to the invention, compared to the prior art method of, for example, U.S. Pat. No. 7,060,986, is that the method according to the invention uses any crystalline sample. Therefore the sample under investigation can be used, and no time is lost or sample introducing process is needed.

The invention is based on the insight that observing the intensity of the spots of the pattern and comparing said intensity distribution with the expected intensity distribution is equivalent to a deconvolution of the beam's cross section. Any asymmetry in the intensity distribution of the pattern indicates an asymmetry of the beam.

The distance from the centre at which spots can be detected indicates the maximum transfer limit in that direction. This shows the need for a symmetric intensity distribution: a symmetric intensity distribution indicates that the transfer limit, or resolution, is identical in all directions. By adjusting the excitation of the correctors the cross section of the beam can be made round, resulting in a symmetric pattern at different defocus values. By observing at which focus value the intensity distribution shows the largest diameter, the best focus value is found.

It is noted that, when the relation between corrector excitation and aberration is known, an 'educated guess' can be made as to how the excitation should be changed, resulting in a fast convergence of the iteration process.

It is noted that a change in the defocus range may be required, or at least helpful, either enlarging the defocus range or making the range smaller.

Preferably the results of the changes in excitation are confirmed by the recording of a HR-STEM image using the new excitation. Should the result thereof in reciprocal space be a symmetric pattern that extends to a sufficiently large diameter (compared to predetermined values), then further changes to the excitation of lens and corrector are not necessary. Should this not be the case, then the image and the representation thereof can be part of the next through-focus series.

Another reason to abort further changes may be that the changes introduced are less than a predetermined value: obviously the end is reached and the process is not converging anymore.

Still another reason to abort further changes may be that a maximum number of iterations is reached: It should be noted that the method according to the invention need not bring the apparatus in the desired state (bring it to a desired high resolution), for example because the resolution of the apparatus is hampered by interferences, such as floor vibrations, acoustical noise, thermal drift, boiling noise in liquid nitrogen dewars, electro-magnetic fields, etc., said interferences sadly well-known to the person skilled in the art. Obviously this is equally true for other known methods.

It is noted that reciprocal space is often referred to as Fourier space, as the Discrete Fourier Transform (of which the Fast Fourier Transform is a special case) is the most used algorithm to determine the representation of an image in reciprocal space. However, other algorithms, such as Discrete Cosine Transform, Discrete Fourier Transform, Discrete Hardaman Transforms, or Power Spectral Density may be used.

It is also mentioned that, as the representation in reciprocal space is only used to determine the maximum spatial resolution in the real image, the process need not be revocable. Should a transform be used that gives reliable results but cannot be used to transform the image in reciprocal space back into real space, this is acceptable for the method according to the invention.

The method according to the invention is well suited to be used on crystalline or poly-crystalline samples. The use of the method can be extended by performing it on a 'calibration' sample, after which the sample is exchanged for a sample to be investigated. This other sample may be crystalline or amorphous.

A preferred embodiment includes performing the method according to the invention on a crystalline or poly-crystalline sample that is mounted on a sample holder together with a sample to be investigated. In this way the method is performed to adjust the corrector, after which the sample holder can be moved such that the sample to be investigated is imaged.

It is mentioned that the method according to the invention is preferably used with a corrector for correcting the spherical aberrations of the objective lens.

It is noted that the method according to the invention can iterate from a state where too much aberrations in the image are present, resulting in an image with limited resolution, to a situation where the aberrations result in an image with a sufficiently high information transfer, even when the exact value of the aberrations or aberration coefficients are not determined.

It is noted that, to avoid a contrast reduction by contamination, a (coma-free) beam shift can be performed so that, for each iteration, the beam is shifted to a fresh and clean area.

It is mentioned that the periodicity of a crystal results in a pattern of dots in reciprocal space. Knowing the crystal in many cases implies that the location of the dots in reciprocal space is known on fore-hand (except for the orientation of the pattern, as this depends on the orientation of the crystal in space). With only some dots detected, the position of all other dots can then be predicted. This eases the search for such dots (in terms of, for example, signal-to-noise), and thus eases determining the periodicity observed in an image, associated with a resolution of said image.

In a preferred embodiment the method makes use of this knowledge, and only evaluates these areas in the representations where a spot is expected.

It is noted that, for reliable operation, the noise level of the representation should be known, so that only peaks with sufficient signal-to-noise ratio are used. The noise level can be determined by, for example, measuring at positions far removed from the centre in reciprocal space where the transfer is essentially zero, or at positions where no 'diffraction' peaks are formed.

In an aspect of the invention a sample carrier for carrying a sample to be analyzed by HR-STEM imaging is characterized in that it comprises a crystalline or poly-crystalline part suited for HR-STEM imaging for performing the method according to any of the preceding claims.

By equipping a sample holder with a crystalline part, the method can be performed on this part and then the sample carrier can be moved such that a sample to be analyzed is imaged.

Preferably the part has a thickness of less than 50 nm, more preferably less than 25 nm, most preferably less than 15 nm, so that no multiple scattering occurs.

A semiconductor material is most suited for the part, as semiconductor materials are widely available, with near-perfect crystals and routine machining methods to make thin crystalline samples thereof.

The invention will now be elucidated in more detail on the basis of exemplary embodiments and the accompanying schematic drawings, in which.

An example of a HR-STEM image and its representation in reciprocal space (Fourier space) is given in, for example, FIG. 4 of the earlier mentioned article by Lupini. Although Lupini uses the obtained representation differently, that is: for determining the local magnification. In his off-axis representations (representations of sub-images) in FIG. 4 slight asymmetry can be observed. This is to be expected for such off-axis images, but also shows the effectiveness of the invention.

The pattern of dots in reciprocal space is the transform of the crystal in reciprocal space ('Fourier space') convoluted with the transform of the beam diameter (the probe profile) in reciprocal space ("Fourier space").

The transform of the crystal is the diffraction pattern, extending to a large distance from the center of the diffraction pattern. For a perfect crystal with infinite dimensions it extends to infinity.

The transform of the beam in reciprocal space is known as the Contrast Transfer Function (CTF). The diameter of the CTF is inversely proportional to the probe diameter, and thus a small probe (with a CTF that extends to a large distance from the center) results in a large area of the diffraction pattern of the crystal to be visible.

It is noted that, when the probe shows N-fold symmetry, the CTF shows N-fold symmetry as well (together with the point symmetry that occurs this may result in a 2N symmetry).

Therefore the relation between probe form and diameter, and thus probe aberrations, to the CTF is clear.

It is further noted that the CTF of a STEM (or more exact: HAADF-STEM) is always positive, without the contrast reversals as occurring in TEM imaging.

It is mentioned that the convolution of the diffraction pattern of the crystal with the CTF results in a pattern of dots with an intensity that is dependent on the CTF and thus drops for increasing distance from the centre.

Figure 1:
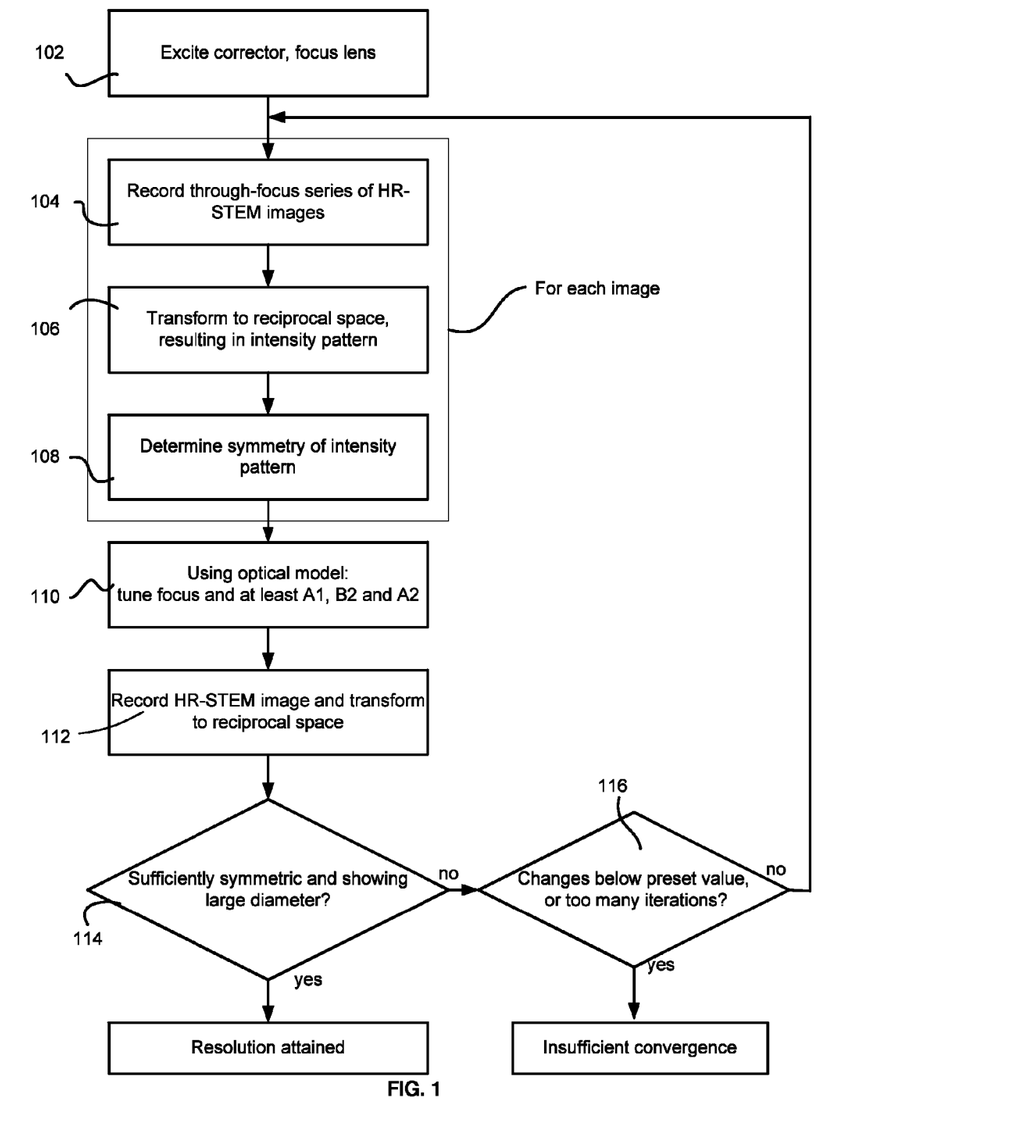
FIG. 1 schematically shows a flowchart of the method.

FIG. 1 schematically shows a flowchart of the method according to the invention.

As a first step 102 the method comprises introducing a crystalline sample in the STEM, focus the objective lens of the STEM to a focal value F and excite the corrector to a first value.

It is noted that focusing the objective lens is a practice that is well-known to an operator of a STEM.

Often an educated guess can be made for the excitation of the corrector, as a result of earlier experiments.

In step 104 a through-focus series of HR-STEM images $I_1 \ldots I_n$ is recorded, in most cases with a defocus value ranging from F−ΔF to F+ΔF (or the other way round), but the range may be asymmetric with respect to F.

In step 106 each of the HR-STEM images $I_1 \ldots I_n$ recorded in the previous step are transformed in reciprocal space, resulting in a series of representation $R_1 \ldots R_n$ of each of the images $I_1 \ldots I_n$. It is noted that many algorithms are known to perform said transformation, of which the Fast Fourier Transform (FFT) is the most well known. The result of such a transform is a pattern of dots, each dot indicating a periodicity occurring in the image. Each observable dot has an intensity with which it extends above the noise level of the representation.

Figure 4:
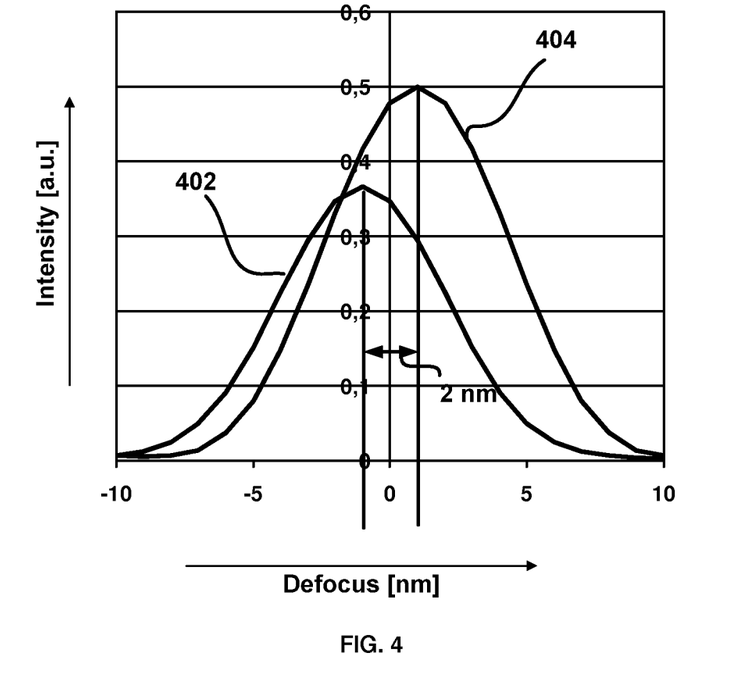
FIG. 4 shows a graph of the relative intensity of the sample as a function of defocus, FIG. 5 schematically shows a TEM grid showing a crystalline part.

In step 108 the symmetry in intensity of the pattern of dots is determined for each of the representations $R_1 \ldots R_n$. Inventors found that two-fold symmetry can be determined by observing in which representation an optimum in one direction occurs and when an optimum in a perpendicular direction occurs, while likewise three-fold symmetry can be determined by comparing dots that are displaced 60 degrees with respect to each other. In the discussion of FIGS. 3 and 4 this method is further explained.

In step 110 the excitation of the objective lens and the corrector are changed, based an optical model for the corrector and the observed asymmetry.

In step 112 a HR-STEM image is recorded, transformed into reciprocal space, and its symmetry and its diameter are evaluated.

In step 114 a decision is made on the basis of symmetry and diameter of the reciprocal image formed in step 112. If this is sufficient (symmetry better than a predetermined value and information limit extended beyond a predetermined value), then the required resolution is present in all directions, and no further tuning of the instrument is needed.

In step 116 another abort criterion is evaluated: although the resolution is not present, there may be a reason why the process does not converge, or does not converge fast enough. Reasons for this may range from interferences (floor- or acoustical vibration, turbulence of cooling water, etc), a bad quality of the crystal (due to, for example, contamination), magnetic stray fields, etc. All this may be a reason to abort the iterative process and "hand-back" control of the instrument to the user.

It is noted that, to avoid deterioration of the sample due to, for example, contamination, it may preferred that the method is performed on another part of the sample than the part to be imaged/analyzed.

It is noted that step 112 is an optional step, and that it may also be decided on, for example, the basis of the magnitude of the change in excitation, whether the image is good enough. In that case the size of the change in excitation can be used to decide to abort the iterations/repetition of steps. This has a larger risk than the embodiment with the optional step 112 before mentioned reasons for lack of convergence may be mistaken as the moment that—sufficient—resolution is reached.

It is noted that, preferably, the optical model and the evaluation of the set of vectors $S_1 \ldots S_n$ lead, if necessary, to a change in excitation of at least focus F, and the combined effect of two-fold astigmatism ($A_1$), coma ($B_2$) and three-fold astigmatism ($A_2$), as the—automatic-setting of these is at the moment limiting (see table 1). However, higher order aberrations can be included in the cooperation of the optical model and the vectors S, and the result is that, when the CTF (corresponding to the beam diameter) is used as an abort criterion (see step 114), the beam diameter/profile is sufficiently small for an image with a resolution that is in all directions better than the required diameter, irrespective of the aberrations that are still present.

It is further noted that this method is not optimized to zero each and every aberration independently, but that instead the combined effect of all aberrations together with the defocus, is minimized.

If possible, the method should be performed on the part of the sample to be analyzed. However, this is not always possible, for example due to the nature of the sample. In that case it is preferred that the method is performed on another part of the sample, or another sample mounted on the same sample carrier, so that the sample to be analyzed need not be introduced into the STEM after performing the method.

This also explains why this method differs fundamentally from observing the diffraction pattern formed in the diffraction plane: as known to the skilled person the diffraction pattern represents the Fourier transform of an image of the sample, but as also known to the skilled person it is formed in the back-focal plane of the objective lens, and imaging this plane on the detector of a microscope requires different settings of the imaging optics, the different settings associated with different aberrations.

It is mentioned that the phrase "analyzed" should, in this context, be interpreted broadly, and includes, for example, imaging.

It is further noted that the aberration corrector may take the form of a corrector of astigmatism, but preferably a corrector of spherical aberration.

Figure 2A:
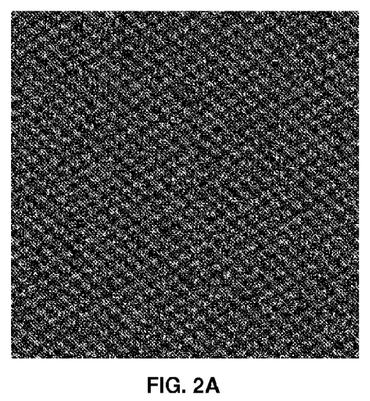
FIGS. 2A-2E show a through-focus series of a Si(110) sample.
Figure 2B:
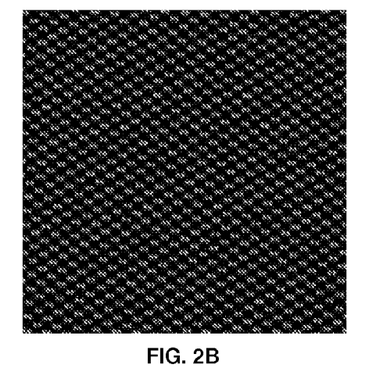
Figure 2C:
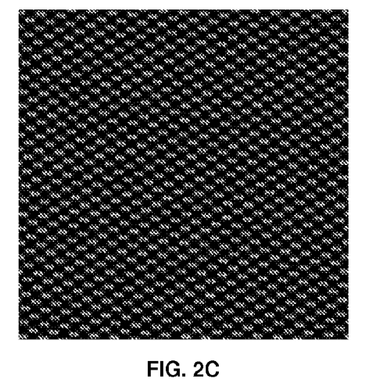
Figure 2D:
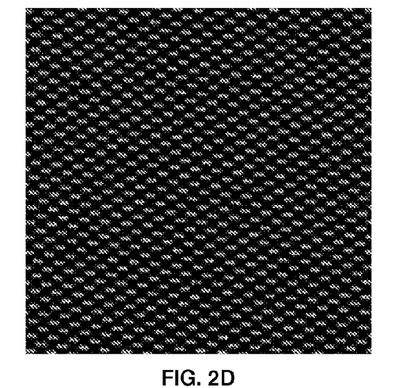
Figure 2E:
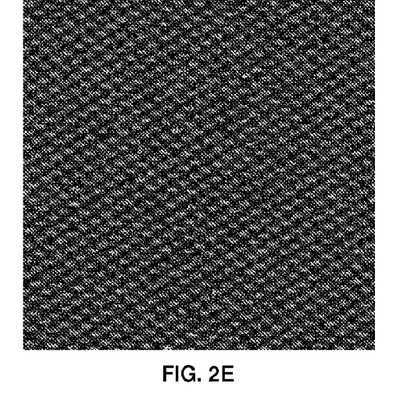
Figure 3A:
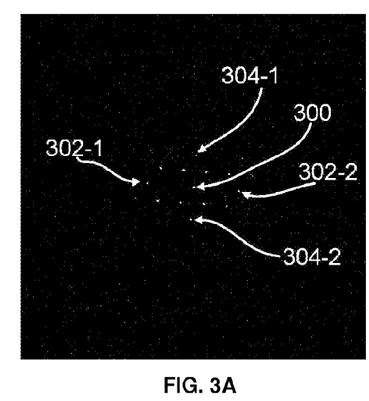
FIGS. 3A-3E show the representations in Fourier Space of FIGS. 2A-2E of the Si(110) sample.
Figure 3B:
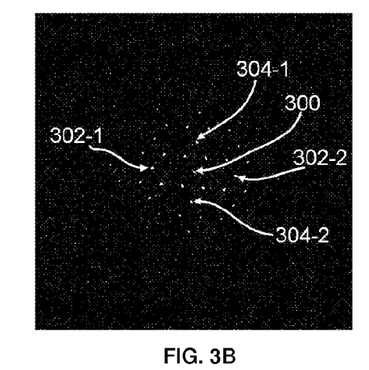
Figure 3C:
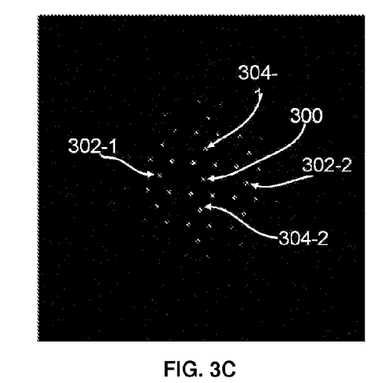
Figure 3D:
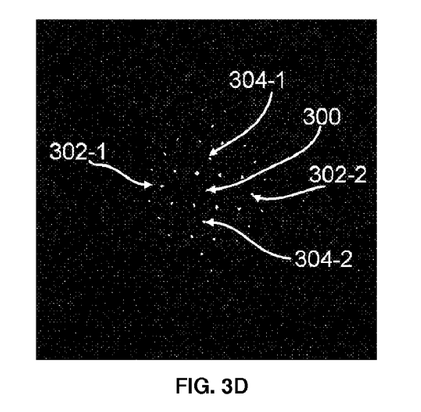
Figure 3E:
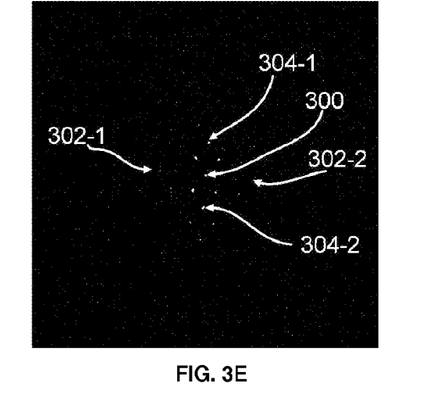

FIGS. 2A-2E show a through-focus series of a Si(110) sample. FIG. 2A shows an image at a defocus of −8 nm, FIG. 2B an image at a defocus of −4 nm, FIG. 2C an image in focus, FIG. 2D an image at a defocus of +4 nm and image 2E an image at a defocus of +8 nm. FIGS. 2A and 2B show astigmatism in a direction proximate to the vertical direction of the image, FIGS. 2D and 2E proximate to the horizontal direction of the image.

FIGS. 3A-3E show the representations of FIGS. 2A-2E of the Si(110) sample, respectively, in Fourier space. The representations form a dot pattern that shows mirror symmetry around the central spot 300. The relative intensity of the spots in the different figures differs, and from this relative intensity in the through-focus series the symmetry is judged. To that end especially spots 302-1 and its mirror inverse 302-2 (the so-called 004 reflections of Si) are monitored, as are spot 304-1 and its mirror inverse 304-2 (the so-called 2-20 reflections of Si).

FIG. 4 shows the relative intensity of spots 302-1 and 302-2 as well as spot 304-1 and 304-2 as a function of defocus. The two curves, curve 402 showing the relative intensity of spots 302-1 and 302-2; and curve 404 showing the relative intensity of spot 304-1 and 304-2, show a maximum at different defocus values. From the thus detected two-fold asymmetry the value and orientation of the two-fold astigmatism is determined.

When the direction of the astigmatism is not known, a larger number of dots can be used under different angular positions. Two of these will show the largest deviation, one in a first direction and the other in a perpendicular direction. This direction now defines the orientation of the astigmatism.

Likewise e.g. three-fold astigmatism can be evaluated by observing three-fold asymmetry (times two, due to the point symmetry) of dots under relative angles of 60 degrees.

It is mentioned that the curves represent the effect of astigmatism and defocus. Therefore the intensity of the dots for large defocus values drops to zero.

It is also mentioned that for optimum results the dot intensity is normalized using the intensity of the central spot.

It is mentioned that the dots used need not be far removed from the center of the pattern: also dots close to the center show intensity variations. It is also not required to compare the variations of dots with comparable intensity: only their orientation is in this respect important.

Figure 5:
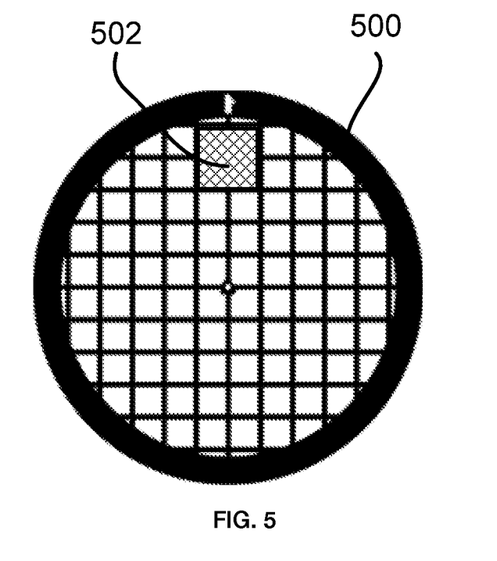

FIG. 5 schematically shows a TEM grid showing a crystalline part.

TEM sample carriers, also known as grids, are known to the person skilled in the art. A standard TEM grid is in most cases a thin copper foil with a diameter of 3.05 mm and a thickness of 25+/−5 μm, although other diameters (e.g. 2 and 3 mm) and thicknesses (e.g. 6+/−2 μm) are known. Also other materials than copper are known, such as gilded copper, nickel, pure gold, gilded nickel, Nylon, carbon, etc. The foils show a perforation in the form of a mesh with a pitch varying from 500 μm to 12.5 μm. A sample is draped over the grid and supported by the bars.

FIG. 5 shows a TEM grid 500, with a crystalline part 502 is included on or in the grid. The crystalline part has, at least locally, a thickness of less than 50 nm, preferably less than 25 nm, most preferable less than 15 nm, as a result of which it is suited for performing the method. Such a crystalline part can be made of semiconductor material, which shows near-perfect crystal quality at an affordable price. However, also other crystals or quasicrystals may be used. If the structural strength of the crystal is insufficient, it may be supported by a thin layer or a thin grid of a material that shows much lower interaction with electrons, such as carbon. In that case a superposition of the two patterns, that of the carbon and the semiconductor material, can be expected.

We claim as follows:

1. A method for adjusting a Scanning Transmission Electron Microscope (STEM), said STEM equipped with an objective lens and an aberration corrector for correcting aberrations of the objective lens, the aberration corrector excited with an excitation, and the objective lens focused to a focal value F, the method comprising the repeated steps of:
    a) recording a through-focus series of high-resolution STEM images $I_1 \ldots I_n$ of a crystalline or poly-crystalline part of a sample, the through-focus series covering a defocus range,
    b) transforming said images to representations $R_1 \ldots R_n$ in reciprocal space, the representations showing a plurality of spots arranged in a pattern, each of the spots showing an intensity, each of the spots indicating a periodicity occurring in the image,
    c) determining for each of the representations $R_1 \ldots R_n$ an asymmetry in intensity distribution of at least part of the spots,
    d) changing the excitation of the aberration corrector and the focal value F based on an optical model of the aberration corrector and the determined asymmetries,
    said repetition of steps aborted when:
        the representation in reciprocal space of an optionally recorded in-focus image shows a symmetry better than a predetermined value and shows a maximum transfer limit higher than a predetermined transfer limit, and/or
        the changes in excitation of the aberration corrector and objective lens are below predetermined values, and/or
        the number of repetitions exceeds a predetermined maximum number of repetitions, the predetermined maximum number of repetitions being greater than one.

2. The method of claim 1 in which the excitation of the aberration corrector is changed to minimize the combined effect of two-fold astigmatism ($A_1$), coma ($B_2$) and three-fold astigmatism ($A_2$).

3. The method of claim 1 in which the reciprocal images $R_1 \ldots R_n$ are formed using a Discrete Cosine Transform, a Discrete Fourier Transform, a Discrete Hardaman Transforms, or a Power Spectrum Density.

4. The method of claim 1 in which the method is performed on a sample to be analyzed.

5. The method of claim 1 in which the method is performed on a sample mounted on a sample carrier together with another sample, the other sample to be analyzed.

6. The method of claim 1 in which the aberration corrector is a corrector of spherical aberration and/or a corrector of astigmatism.

7. The method of claim 1 in which the images are recorded of different parts of the sample so as to avoid contamination.

8. The method of claim 1, further comprising the repeated step of changing the defocus range.

9. The method of claim 1, further comprising the repeated step of recording a high-resolution STEM image using the altered values of excitation and/or focus, transform said image to a representation in reciprocal space and determine the symmetry of said representation as well as the distance from the centre of the pattern at which spots can be observed, said distance giving an indication of the maximum transfer limit.

* * * * *